US 6,649,755 B1

(12) United States Patent
Hong et al.

(10) Patent No.: US 6,649,755 B1
(45) Date of Patent: Nov. 18, 2003

(54) PROCESS FOR PREPARING ACARBOSE WITH HIGH PURITY

(75) Inventors: Chung Il Hong, Chicago, IL (US); Kyung Hwan Kim, Seoul (KR); Byoung Taik Choi, Seoul (KR); Gang Sun Choi, Kyunggi-do (KR); Yong Rack Choi, Seoul (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 10/111,636

(22) PCT Filed: Sep. 25, 2000

(86) PCT No.: PCT/KR00/01068

§ 371 (c)(1),
(2), (4) Date: Apr. 26, 2002

(87) PCT Pub. No.: WO01/30796

PCT Pub. Date: May 3, 2001

(30) Foreign Application Priority Data

Oct. 28, 1999 (KR) .......................... 1999-47093

(51) Int. Cl.⁷ ................................. C07H 5/06
(52) U.S. Cl. .................... 536/127; 536/17.2; 536/18.7; 536/55.3
(58) Field of Search ................. 536/17.2, 55.3, 536/127, 18.7; 514/35, 23; 424/115; 428/402

(56) References Cited

U.S. PATENT DOCUMENTS

| 3,876,766 A | | 4/1975 | Frommer et al. ........... 424/115 |
| 3,879,546 A | | 4/1975 | Frommer et al. ........... 424/115 |
| 4,019,960 A | | 4/1977 | Frommer et al. ........... 424/115 |
| 4,062,950 A | | 12/1977 | Frommer et al. ............. 514/35 |
| 4,174,439 A | * | 11/1979 | Rauenbusch et al. ...... 536/55.3 |
| 4,666,776 A | * | 5/1987 | Lange et al. ................. 428/402 |
| 4,767,850 A | * | 8/1988 | Lange et al. ................. 536/127 |
| 4,904,769 A | * | 2/1990 | Rauenbusch ............... 536/17.2 |

FOREIGN PATENT DOCUMENTS

| IT | WO 99/07720 | * | 2/1999 | .......... C07H/15/00 |
| WO | 9907720 | | 2/1999 | .......... C07H/15/00 |

* cited by examiner

*Primary Examiner*—James O. Wilson
*Assistant Examiner*—Ganapathy Krishnan
(74) *Attorney, Agent, or Firm*—Webb Ziesenheim Logsdon Orkin & Hanson, P.C.

(57) ABSTRACT

Disclosed herein is a process for preparing highly pure acarbose of formula (I) useful as medicine for the treatment of diabetes. The disclosed process comprises prepurifying an acarbose-containing solution using a synthetic adsorbent to produce a prepurified acarbose having an acarbose content of a predetermined level or more; and contacting the prepurified acarbose with a monodispersed, strongly acid cation exchanger, in one step, to absorb acarbose.

10 Claims, No Drawings

PROCESS FOR PREPARING ACARBOSE WITH HIGH PURITY

BACKGROUND OF THE INVENTION

1. Field of the Invention

The present invention relates in general to a process for preparing acarbose with high purity useful as medicine for the treatment of diabetes. More particularly, it relates to a process for preparing acarbose with high purity represented by the formula (I), which comprises prepurifying an acarbose-containing solution using a synthetic adsorbent to produce a prepurified acarbose having an acarbose content of a predetermined level or more; and contacting the prepurified acarbose with a monodispersed, strong acid cation exchanger, in one step, to adsorb acarbose.

Meanwhile, as disclosed in U.S. Pat. No. 4,174,439, the fermentation broth containing mycelium is introduced with the strong acid cation exchanger and the anion exchanger to adsorb acarbose on the exchangers. The mixed ion exchange resin is then separated off from the mycelium by a sieve screw. The mixed ion exchange resin is rinsed with distilled water, and introduced into a first column. Then, the acarbose mixture adsorbed on the column is eluted with a diluted hydrochloric acid. The resulting eluate is passed through a second column whose lower layer portion is packed with an anion exchanger and whose upper layer portion is packed with a highly crosslinked, strong acid cation exchanger. The eluate from the second column is further adsorbed on a strong acid cation exchanger which is then rinsed with a small amount of distilled water. The cation exchanger is fractionally eluted with a diluted hydrochloric acid. The active fractions are neutralized with an anion exchanger,

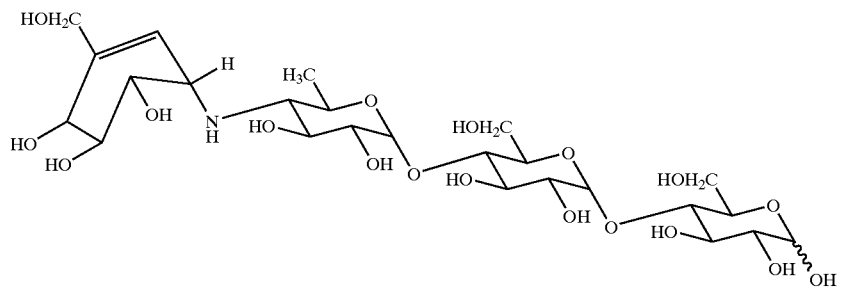

(I)

2. Description of the Prior Art

Acarbose as a glucosidase inhibitor reduces the glucose level in human blood by delaying the absorption of glucose in the human small intestine and thus widely used in medicine for the treatment of diabetes. The inhibitor is obtained by fermentation of Actinoplanes species (see German Patent No. 2,209,832; German Patent No. 2,209,834; and German Patent No. 2,064,092). Many methods for isolating acarbose from this fermentation broth are known in the art.

As disclosed in U.S. Pat. No. 4,062,950, the fermentation broth containing acarbose is centrifuged and the resulting supernatant is decolorized with active charcoal or nonspecific adsorption resins under acid condition, and adsorbed onto active charcoal under neutral condition to separate off ionic materials. After the adsorbed material is eluted with an alcoholic solution or an acetone-containing solution under acidic condition, the eluate is bound to a strong acid cation exchanger or a weak acid cation exchanger. The resulting exchanger is then eluted with an acidic or basic aqueous solution. The eluted solution is then neutralized with an ion exchanger resin and concentrated in vacuo. Then, the concentrate is lyophilized or crystallized by precipitation in organic solvents. At this time, the content of acarbose is 85% in the dry matter(by HPLC method). To prepare acarbose in the more pure state, the crystalline acarbose is then redissolved in distilled water and chromatographed on an ion exchanger resin using cellulose as a substrate. Then, the resulting active fractions are collected and concentrated, followed by lyophilization or precipitation in organic solvents. However, the method disclosed in the latter patent is disadvantageous in that it includes the use of active charcoal and the use of expensive ion exchangers in several steps and thus involves a complicated process and a large economical burden.

concentrated in vacuo, sterilized by filtration and freeze-dried or spray-dried to afford acarbose at a yield of 52% to 58% in the dry matter.

Meanwhile, as disclosed in U.S. Pat. Nos. 4,666,776 and 4,767,850, the acarbose-containing eluate recovered from the steps 1–5 of U.S. Pat. No. 4,174,439 is adsorbed on a strong acid cation exchanger which is then rinsed with a small amount of distilled water. The resulting eluate is chromatographed using a diluted hydrochloric acid. Then, the active fractions are neutralized with an anion exchanger and lyophilized to give acarbose at an interval yield of 79 to 82%. The obtained acarbose is 78 to 88% pure (by HPLC method).

The prior purification methods as described above utilize complex process in which a step using a combination of the cation exchanger and the anion exchanger is repeatedly performed and a chromatographic step using the cation exchanger is further conducted. Nevertheless, acarbose purified according to these prior methods show an acarbose content unsuitable for use in human medicine.

U.S. Pat. No. 4,904,769 discloses a method of preparing highly pure acarbose from an acarbose-containing solution prepurified according to known methods. The disclosed method utilizes as packing material an expensive, weak acid cation exchanger which has carboxyl groups and is based on dextran, agarose and cellulose. Also, this method maintains the pH of equilibration of the packing material and the constant temperature during the chromatography. This method provide acarbose having a content of not less than 90% by weight at an interval yield of 82% or more. However, this method is disadvantageously more complex in purification process by using the acarbose-containing solution prepurified according to the known methods and further using the weak acid cation exchanger. In addition, this method disadvantageously involves a large economical burden due to the use of the expensive ion exchanger.

PCT Publication WO 99/07720 discloses a method which includes prepurifying an acarbose in fermentation broth by methods discribed in U.S. Pat. Nos. 4,062,950, 4,767,850 and 4,904,769 and then recovering acarbose having a content of not less than 98% using a non-aromatic, strong acid cation exchanger. However, such a method is likewise complex in purification process since it utilizes an acarbose-containing solution prepurified according to the known technologies. Also, this method involves a high economical burden upon its industrial application as it utilizes the expensive, non-aromatic strong acid cation exchanger.

SUMMARY OF THE INVENTION

We have conducted a study on purification method in an attempt to overcome problems of the process complexity and thus the large economical burden. As a result, we have found that an acarbose-containing solution is prepurified using a synthetic adsorbent to obtain a prepurified acarbose having a content of a predetermined level or more, and then highly pure acarbose useful as medicine for the treatment of diabetes is recovered from the prepurified acarbose with only a monodispersed, strong acid cation exchanger, instead of the use of an expensive, weak acid cation exchanger. On the basis of this discovery, we have completed the present invention.

The present invention is a method capable of omitting the use of active charcoal and the five to six steps-exchanger resin process as carried out in the prior method. This method produces highly pure acarbose by prepurifying an acarbose-containing solution with a synthetic adsorbent and then contacting the prepurified acarbose with a monodispersed, strong acid cation exchanger, in one step, to adsorb acarbose.

Generally, due to cation materials other than acarbose present in a filtrate obtained by filtration of mycelium from a fermentation broth, the adsorption of acarbose to a cation exchanger does not easily occur. For this reason, instead of the use of active charcoal and a large amount of ion exchangers as in the prior, the method of the present invention utilizes a synthetic adsorbent to remove coloring materials and impurities other than acarbose and analogues thereof in an acarbose-containing solution. The synthetic adsorbent used in the method of the present invention is selected from the group consisting of a highly porous styrene polymer, a highly porous styrene polymer having bromine chemically bound thereto, a highly porous styrene/divinyl polymer, a crosslinked macroporous aliphatic polymer, a crosslinked macroporous aromatic polymer, a metacrylic acid-based synthetic adsorbent, a carbonaceous synthetic adsorbent which is highly porous and based on a styrene/divinylbenzene ion exchange resin. Example of the synthetic adsorbent that can be used in the practice of the present invention include DIAION™ SP207, SP700, SP825, SP850, HP20, HP21 and HP2MG commercially available from Mitsubishi Chemical Co.; AMBERLITE™ XAD4, XAD7, XAD16, and XAD1600T commercially available from Rohm and Hass Co.; AMBERSORB™ 563, 572, and 600 commercially available from Rohm and Hass Co.; and Lewatit™ VP OC 1064, VP OC 1066 and EP 63 commercially available from Bayer Co.

The resulting synthetic adsorbent containing acarbose is then washed with distilled water and acarbose is eluted from the synthetic adsorbent using a pH-adjusted liquid solution or an organic solvents. Then, the acarbose-containing eluate is passed through an anion exchanger at a high flow rate to be decolorized and neutralized. Examples of the anion exchanger used include DIAION™ SA11A commercially available from Mitsubishi Chemical Co.; AMBERLITE™ IRA67 commercially available from Rohm and Haas Co.; and Lewatit™ MP 64 commercially available from Bayer Co. Subsequently, the resulting eluate is contacted with a monodispersed, strong acid cation exchanger to adsorb acarbose on the cation exchanger. The monodispersed, strong acid cation exchanger used in the method of the present invention is a crosslinked polystyrene-based gel-type agent containing a sulfate group in the form of a bead-shaped monodisperse resin packed in a hexagonal bed structure. Also, the cation exchanger has a particle size of 0.15 to 0.3 mm and preferably 0.21 to 0.25 mm. Examples of the cation exchanger include MFG 210 and MFG 250 commercially available from Finex Co. Then, the eluate is chromatographed with a diluted hydrochloric acid to remove the remaining salts, sugar-containing basic secondary components, and acarbose analogues, etc. Thus, the method of the present invention enables the preparation of acarbose having a high purity of not less than 98% by the three-step resin process.

DETAILED DESCRIPTION OF THE PREFERRED EMBODIMENTS

The pH of an acarbose-containing solution obtained by filtration of a fermentation broth is adjusted to 3–9 and preferably 5–7. The pH-adjusted solution is introduced into a synthetic adsorbent and the adsorbed acarbose is eluted with distilled water of pH 1 to 5 (preferably, pH 1 to 3) or eluted with alcohol- or acetone-containing distilled water (preferably, 5–30% acetone solution). The resulting acarbose-containing eluate shows a purity of not less than 50% (by HPLC method). Then, the eluate is passed through anion exchanger at a high flow rate to be decolorized and neutralized. The resulting eluate is contacted with a strong acid cation exchanger to adsorb acarbose and subsequently washed with a small amount of distilled water. The most critical factor to isolate acarbose adsorbed on the strong acid cation exchanger is the pH of the eluent being applied. For this reason, acarbose is eluted from the strong acid cation exchanger with distilled water of pH 1.0–3.0 to give highly pure acarbose having a purity of not less than 98%. The elution is preferably carried out with distilled water of pH 1.5–2.5. More preferably, after sugar-like components are eluted with distilled water of pH 2.1–2.5, highly pure acarbose is rapidly eluted with distilled water of pH 1.5 to 2.1.

The method of the present invention is simple in process as compared to that of the prior methods, and particularly enables the preparation of a prepurified acarbose having a purity of not less than 50% (the HPLC method) by use of the synthetic adsorbent instead of active charcoal and ion exchange resin in five to six steps. Also, the method of the present invention can simply isolate and recover acarbose having a purity of not less than 98% (by HPLC method) from the prepurified acarbose using a cheaper, strong acid cation exchanger without using the expensive, weak acid cation exchanger.

The present invention is further described by referring to the following examples. However, the present invention should not be understood to be limited to the examples.

EXAMPLE 1

A chromatography column of diameter 4 cm and length 12 cm was packed with 150 ml of Lewatit™ EP 63 (Bayer Co.), a synthetic adsorbent. The test material used was 150 ml of a culture filtrate containing about 0.25 g of acarbose.

The filtrate was adjusted to pH 5 and applied to the column at a flow rate of 2.3 ml/min. The column was washed with distilled water at room temperature and eluted with distilled water containing 10% acetone. The main fraction was then combined to give a solution containing 0.2 g of acarbose (acarbose content of 50.1% by HPLC method). The column was regenerated with 200 ml of 1M sodium hydroxide solution and washed with 400 ml of distilled water.

EXAMPLE 2

A chromatography column of diameter 2.5 cm and length 8 cm was packed with 20 ml of AMBERLITE™ IRA 67 (Rohm and Hass Co.), an anion exchanger. The test material used was 70 ml of a solution containing 0.2 g of acarbose which had been prepurified according to Example 1. The test substance was applied to the column at a flow rate of 3.5 ml/min. Then, the column was washed with distilled water to give 96 ml of a decolorized and neutralized solution containing 0.2 g of acarbose.

EXAMPLE 3

A chromatography column of diameter 4 cm and length 12 cm was packed with 150 ml of AMBERLITE™ XAD 1600T (Rohm and Hass Co.), a synthetic adsorbent. The test material used was 300 ml of a culture filtrate containing about 0.45 g of acarbose. The filtrate was adjusted to pH 5 and applied to the column at a flow rate of 2.3 ml/min. The column was washed with distilled water at room temperature and eluted with distilled water containing 10% acetone. The main fraction was combined and resulted in a solution containing 0.4 g of acarbose (acarbose content of 52% by HPLC method). The column was regenerated with 200 ml of 1M sodium hydroxide solution and washed with 400 ml of distilled water. The resulting acarbose-containing solution was passed through AMBERLITE™ IRA 67 (Rohm and Hass Co.) according to the method described in Example 2 to give 95 ml of a decolorized and neutralized solution containing 0.39 g of acarbose.

EXAMPLE 4

A chromatography column of diameter 6 cm and length 40 cm was packed with 1 L of DIAION™ SP850 (Mitsubishi Chemical Co.), a synthetic adsorbent. The test substance used was 3 L of a culture filtrate containing about 3.9 g of acarbose. The filtrate was adjusted to pH 5 and applied to the column at a flow rate of 16.7 ml/min. The column was washed with distilled water at room temperature and eluted with distilled water containing 10% acetone. The main fraction was combined to give a solution containing 3.5 g of acarbose (acarbose content of 50.7% by HPLC method). The column was regenerated with 1 L of 1M sodium hydroxide solution and washed with 2 L of distilled water. The resulting acarbose-containing solution was passed through AMBERLITE™ IRA 67 (Rohm and Hass Co.) according to the method described in Example 2 to give 750 ml of a decolorized and neutralized solution containing 3.5 g of acarbose.

EXAMPLE 5

A chromatography column of diameter 6 cm and length 40 cm was packed with 1 L of DIAION™ SP207 (Mitsubishi Chemical Co.), a synthetic adsorbent. The test substance used was 10 L of a culture filtrate containing about 4.9 g of acarbose. The filtrate was adjusted to pH 5 and applied to the column at a flow rate of 15.2 ml/min. The column was washed with distilled water at room temperature and eluted with distilled water of pH 1. The main fraction was then combined to give a solution containing 4.2 g of acarbose (acarbose content of 69% by HPLC method). The column was regenerated with 1 L of 1M sodium hydroxide solution and washed with 2 L of distilled water. The resulting acarbose-containing solution was passed through AMBERLITE™ M IRA 67 (Rohm and Hass Co.) according to the method described in Example 2 to give 660 ml of a decolorized and neutralized solution containing 4.1 g of acarbose.

EXAMPLE 6

A chromatography column of diameter 3.5 cm and length 40 cm was packed with 200 ml of MFG 210 (Finex Co.), a strong acid cation exchanger. The test substance used was 750 ml of a solution containing 3.5 g of acarbose, which had been prepurified in Example 4. The test substance was applied to the column at a flow rate of 3.3 ml/min. The column was then washed with distilled water at room temperature. The column was eluted with distilled water of pH 2.1 to elute sugar-like secondary components and then eluted with distilled water of pH 2.0 at a point of time at which acarbose was eluted. The main fraction was combined to give a solution containing 2.7 g of acarbose (acarbose content of 98.1% by HPLC 15 method).

EXAMPLE 7

A chromatography column of diameter 3.5 cm and length 40 cm was packed with 200 ml of MFG 250 (Finex Co.), a strong acid cation exchanger. The test substance used was 500 ml of a solution containing about 3.1 g of acarbose, which had been prepurified in Example 5. The test substance was applied to the column at a flow rate of 3.1 ml/min. The column was then washed with distilled water at room temperature. The column was eluted with distilled water of pH 2.1 to elute sugar-like secondary components and then eluted with distilled water of pH 2.0 at a point of time at which acarbose was eluted. The main fraction was combined to give a solution containing 2.4 g of acarbose (acarbose content of 98.7% by HPLC 30 method).

As apparent from the foregoing, the present invention provides the method capable of preparing acarbose useful in medicine for the treatment of diabetics at a high purity of not less than 98% by only a simple three-step exchanger resin process without using complex purification processes. This method includes prepurifying an acarbose-containing solution using a synthetic adsorbent instead of active charcoal and five to six steps-ion exchanger resin process, to produce a prepurified acarbose solution having an acarbose content of a predetermined level or more; and recovering highly pure acarbose with only a strong acid cation exchanger in one step. Therefore, the method of the present invention can reduce purification costs and also purification time and thus is industrially and economically advantageous.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A process for preparing highly pure acarbose having an acarbose content of not less than 98%, which comprises the steps of:

filtering an acarbose-containing fermentation culture;

adjusting the pH of the filtrate to 3–9;

contacting the pH-adjusted filtrate with a synthetic adsorbent to adsorb acarbose;

eluting the adsorbed acarbose with one of distilled water of pH 1–5 and acetone-containing distilled water;

passing the resulting eluate through an anion exchanger at a high flow rate to decolorize and neutralize the eluate;

contacting the eluate with a monodispersed, strong acid cation exchanger to adsorb acarbose; and eluting the adsorbed acarbose with distilled water of pH 1.0–3.0, thereby yielding the highly pure acarbose.

2. The process according to claim 1, wherein the synthetic adsorbent is selected from the group consisting of a highly porous styrene polymer, a highly porous styrene polymer having bromine chemically bound thereto, a highly porous styrene/divinylbenzene polymer, a crosslinked macroporous aliphatic polymer, a crosslinked macroporous aromatic polymer, a methacrylic acid-based synthetic adsorbent, a carbonaceous synthetic adsorbent which is highly porous and based on styrene/divinylbenzene ion exchange resin.

3. The process according to claim 1, wherein the acarbose adsorbed on the synthetic adsorbent is eluted with one of distilled water containing 5–30% acetone and distilled water of pH 1 to 3.

4. The process according to claim 3, wherein the eluate eluted from the synthetic adsorbent has an acarbose content of not less than 50%.

5. The process according to claim 1, wherein the strong acid cation exchanger is a crosslinked polystyrene-based gel-type agent containing a sulfate group having a particle size of 0.15 to 0.3 mm which is in the form of a bead-shaped monodisperse resin packed in a hexagonal bed structure.

6. The process according to claim 5, wherein the acarbose adsorbed on the strong acid cation exchanger is eluted with distilled water of pH 2.0 after sugar-like components are eluted with distilled water of pH 2.1.

7. The process according to claim 2, wherein the acarbose adsorbed on the synthetic adsorbent is eluted with one of distilled water containing 5–30% acetone and distilled water of pH 1 to 3.

8. The process according to claim 7, wherein the eluate eluted from the synthetic adsorbent has an acarbose content of not less than 50%.

9. The process according to claim 2, wherein the strong acid cation exchanger is a crosslinked polystyrene-based gel-type agent containing a sulfate group having a particle size of 0.15 to 0.3 mm which is in the form of a bead-shaped monodisperse resin packed in a hexagonal bed structure.

10. The process according to claim 9, wherein the acarbose adsorbed on the strong acid cation exchanger is eluted with distilled water of pH 2.0 after sugar-like components are eluted with distilled water of pH 2.1.

* * * * *

UNITED STATES PATENT AND TRADEMARK OFFICE
CERTIFICATE OF CORRECTION

PATENT NO. : 6,649,755 B1 Page 1 of 1
DATED : November 18, 2003
INVENTOR(S) : Chung II Hong et al.

It is certified that error appears in the above-identified patent and that said Letters Patent is hereby corrected as shown below:

Column 6,
Line 8, reads " M IRA" should read -- IRA --.
Line 27, reads "HPLC 15 method" should read -- HPLC method --.
Line 42, reads "HPLC 30 method" should read -- HPLC method --.

Signed and Sealed this

Eighteenth Day of May, 2004

JON W. DUDAS
*Acting Director of the United States Patent and Trademark Office*